US008493286B1

(12) United States Patent  
Agrama

(10) Patent No.: US 8,493,286 B1
(45) Date of Patent: Jul. 23, 2013

(54) FACIAL MOVEMENT MEASUREMENT AND STIMULATION APPARATUS AND METHOD

(76) Inventor: Mark T. Agrama, Palm Beach Gardens, FL (US)

( * ) Notice: Subject to any disclaimer, the term of this patent is extended or adjusted under 35 U.S.C. 154(b) by 1036 days.

(21) Appl. No.: 12/427,739

(22) Filed: Apr. 21, 2009

(51) Int. Cl.
*G09G 5/00* (2006.01)

(52) U.S. Cl.
USPC .............................................. 345/8; 382/118

(58) Field of Classification Search
USPC .............. 345/8, 9, 156; 382/117, 118; 348/77
See application file for complete search history.

(56) References Cited

U.S. PATENT DOCUMENTS

| | | | |
|---|---|---|---|
| 4,641,645 A | 2/1987 | Tayebi | |
| 5,689,575 A | 11/1997 | Sako et al. | |
| 5,801,763 A * | 9/1998 | Suzuki | 348/77 |
| 6,031,539 A | 2/2000 | Kang et al. | |
| 6,064,390 A | 5/2000 | Sagar et al. | |
| 6,072,496 A | 6/2000 | Guenter et al. | |
| 6,121,953 A | 9/2000 | Walker | |
| 6,606,096 B2 | 8/2003 | Wang | |
| 6,664,956 B1 | 12/2003 | Erdem | |
| 7,379,071 B2 | 5/2008 | Liu et al. | |
| 7,383,181 B2 * | 6/2008 | Huang et al. | 704/231 |
| 7,450,126 B2 | 11/2008 | Marschner et al. | |
| 8,098,273 B2 * | 1/2012 | Khouri et al. | 348/14.1 |
| 2008/0050999 A1 | 2/2008 | Jang et al. | |
| 2008/0218472 A1 | 9/2008 | Breen et al. | |

* cited by examiner

*Primary Examiner* — Abbas Abdulselam
(74) *Attorney, Agent, or Firm* — Gold & Rizvi, P.A.; Glenn E. Gold

(57) ABSTRACT

An illustrative embodiment of a facial movement measurement and stimulation apparatus includes at least one facial movement sensor adapted to sense facial movement in a subject and a device interfacing with the facial movement sensor or sensors and adapted to receive at least one signal from the facial movement sensor or sensors and indicate facial movement of the subject. A facial movement measurement and stimulation method is also disclosed.

18 Claims, 9 Drawing Sheets

FACIAL MOVEMENT MEASUREMENT AND STIMULATION APPARATUS AND METHOD

FIELD OF THE INVENTION

The present disclosure generally relates to apparatuses and methods for measuring movement of facial muscles. More particularly, the present disclosure relates to a facial movement measurement and stimulation apparatus and method for measuring and/or stimulating movement of facial muscles in the display of facial expressions.

BACKGROUND OF THE INVENTION

Facial expressions, while displayed by many animal species, are most highly developed in primates and most particularly in humans. Although humans have developed a great capacity to communicate using verbal language, the role of facial expressions in interpersonal interactions remains substantial. Facial expressions provide a means of understanding a person's innermost thoughts and emotions which may defy interpretation by verbal means alone. Therefore, facial expressions in combination with verbal expressions tend to more accurately convey the intended thoughts, feelings and intentions of a person than can be conveyed through verbal expressions only. Moreover, facial expressions and the underlying emotions of which they are a manifestation tend to be contagious, as a person who sees a smiling person is likely to embrace and reflect the positive emotions of that person by smiling as well.

Restoration of a person's lost ability to properly express his or her thoughts and emotions through facial expressions or training of a person in mimicking facial expressions may be desirable in a variety of contexts. In some cases, the ability of a person to express his or her underlying thoughts and emotions accurately through appropriate facial expressions, or the ability of a person to change facial expressions according to changing thoughts and emotions, may diminish or disappear due to causes such as disease, accident or drug abuse, for example. Additionally, actors-in-training may encounter challenges in reacting to staged situations with appropriate facial expressions which may be more naturally assumed by persons who encounter the actual situations.

Therefore, a facial movement measurement and stimulation apparatus for measuring and/or stimulating movement of facial muscles and which is amenable to a variety of applications is needed.

SUMMARY OF THE INVENTION

The present disclosure is generally directed to a facial movement measurement and stimulation apparatus and method for measuring and/or stimulating movement of facial muscles in a variety of applications. In some applications, the apparatus and method may determine a person's ability to assume facial expressions by measuring the electrical activity or movement of the person's facial muscles. In some applications, the apparatus and method may be implemented in a therapeutic context in which a person is trained to assume facial expressions that accurately reflect the person's underlying thoughts and emotions or the person is trained to change facial expressions to accurately reflect the person's changing thoughts and emotions. In some applications, the apparatus and method may be used to train a person in mimicking facial expressions in response to staged situations. In some applications, the goals of the apparatus and method may be implemented by facilitating the sharing or transfer of facial expressions between two or more subjects.

In some embodiments, the facial movement measurement and stimulation apparatus may include:
- at least one facial movement sensor adapted to sense facial movement in a subject; and
- a device interfacing with the facial movement sensor and adapted to receive at least one signal from the facial movement sensor and indicate facial movement of the subject.

In another aspect, the at least one facial movement sensor may include at least one electrode.

In still another aspect, the at least one facial movement sensor may include at least one accelerometer.

In yet another aspect, the device may include a video game console.

In a still further aspect, the facial movement sensor or sensors may be provided on a mask.

In another aspect, at least one electrode may interface with the device and the device may be adapted to transmit at least one electrical impulse to the at least one electrode.

In another aspect, one or more low level electrical impulses may, instead of causing firing of the muscles, be provided to cause sensory stimulation as a means for regulating emotions.

In a still further aspect, the at least one facial movement sensor may be provided on a first mask and the at least one electrode may be provided in a second mask.

In yet another aspect, the at least one facial movement sensor may interface with the device through wiring.

In another aspect, the at least one facial movement sensor may interface with the device wirelessly.

In still another aspect, the device may include a computer having a display and the computer may be adapted to indicate facial movement of the subject on the display.

In yet another aspect, the computer may be adapted to present a facial image on the display and present at least one facial movement indication on the facial image.

In another aspect, the at least one facial movement sensor may include a plurality of facial movement sensors.

In still another aspect, the facial expression and the stimulation can be treated as a feedback loop that can be monitored and regulated.

BRIEF DESCRIPTION OF THE DRAWINGS

The invention will now be described, by way of example, with reference to the accompanying drawings, where like numerals denote like elements and in which.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure which is defined by the claims. Furthermore, there is no intention to be bound by any expressed or implied theory presented in the preceding technical field, background, brief summary or the following detailed description.

The present disclosure is generally directed to a facial movement measurement and stimulation apparatus and method for measuring and/or stimulating movement of facial muscles in a variety of applications. In some applications, the apparatus and method may determine a person's ability to make facial movements or assume facial expressions by measuring the electrical activity or movement of the person's facial muscles. In some applications, the apparatus and method may be implemented in a therapeutic context in which a person is trained to assume facial expressions that accurately reflect the person's underlying thoughts and emotions or the person is trained to change facial expressions to accurately reflect the person's changing thoughts and emotions. Alternatively, the stimulation can be provided at a low enough level to cause sensory stimulation without causing firing of the muscles. In some applications, the apparatus and method may be used to train a person in mimicking facial expressions in response to staged situations. In some applications, the goals of the apparatus and method may be attained by facilitating the sharing or transfer of facial movements or expressions between two or more subjects.

Figure 1:
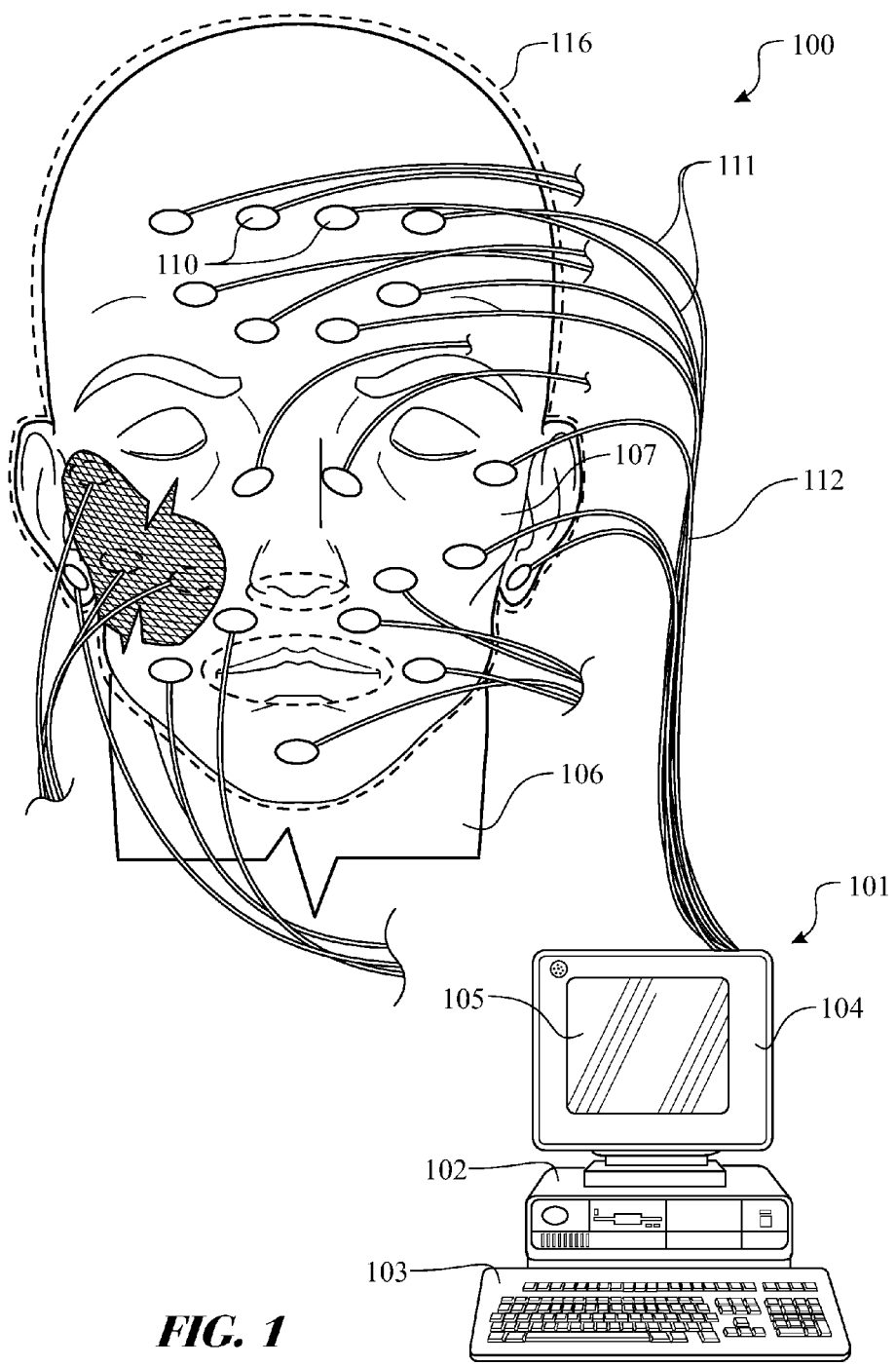
FIG. 1 is a front view of an illustrative embodiment of the facial movement measurement and stimulation apparatus (partially in section), with multiple electrodes attached to a face of a subject (shown in section) in typical implementation of the apparatus.
Figure 2:
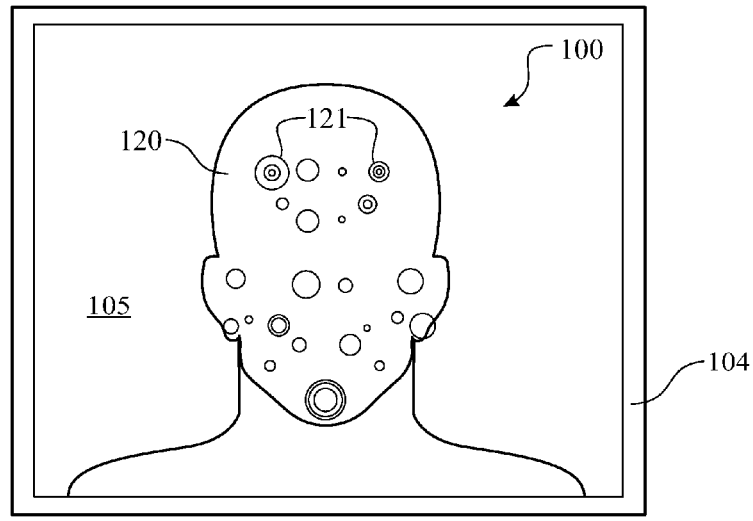
FIG. 2 is a front view of a computer monitor of an illustrative embodiment of the apparatus, with a facial image of the subject presented on the monitor and multiple facial movement indications presented on the facial image and indicating movement of the subject's facial muscles in the locations which correspond to the facial movement indications.

Referring initially to FIGS. 1 and 2 of the drawings, an illustrative embodiment of the facial movement measurement and stimulation apparatus, hereinafter apparatus, is generally indicated by reference numeral 100 in FIG. 1. In some applications, the apparatus 100 may function as an electromyographic measurement system to measure movements of facial muscles (not illustrated) in the face 107 of a subject 106 for any of a variety of purposes. For example, lack or impairment of movement of the facial muscles in the face 107 of the subject 106, as interpreted by the apparatus 100, may reveal a medical condition (such as facial paralysis due to a stroke, for example) and provide the basis for a medical diagnosis and/or therapeutic treatment regimen for the medical condition. Accordingly, the apparatus 100 may include multiple electrodes 110, which in some applications may function as facial movement sensors that may be placed on the skin (not illustrated) at various locations on the face 107 of the subject 106 to measure movement of the musculature (not illustrated) in the face 107. The locations of the electrodes 100 may correspond in position to individual muscles (not illustrated) of the facial musculature, which underlies the skin in the face 107. In some applications, the electrodes 100 may be confined to a portion of the face 107. In some applications, the electrodes 100 may be placed over the entire face 107 and may additionally or alternatively be placed on one or both ears and/or along the neck and larynx of the subject 106. Each electrode 100 may be adapted to measure both sporadic or continuous high-level electrical nerve stimulation and continuous, low-level electrical nerve stimulation of the muscles in the face 107.

In some embodiments, each electrode 100 may be directly affixed to the face 107 of the subject 106 using a suitable adhesive. In other embodiments, the system 100 may include a flexible or stretchable mask 116, which conforms to the features on the face 107. The electrodes 110 may be provided on a contact surface (not illustrated) of the mask 116 with the skin on the face 107. Adhesive (not illustrated) may be provided on the contact surface of the mask 116 to facilitate adhesion of the mask 116 to the skin on the face 107 and maintain electrically-conductive contact between the electrodes 110 and the skin on the face 107. In some embodiments, the electrodes 110 may be surgically implanted in the skin at the desired locations on the face 107.

The system 100 may further include a computer 101 which in some embodiments may be connected to the electrodes 110 through electrode wiring 111. The electrode wiring 111 may be wrapped in a wiring bundle 112. In other embodiments, the electrodes 110 may interface with the computer 110 through wireless transmissions 130 (FIG. 3), according to the knowledge of those skilled in the art. The computer 101 may be conventional and may include a computer disk drive 102 with a computer keyboard 103 and a computer monitor 104 having a display 105 connected to the computer disk drive 102. In applications in which the electrodes 110 function as facial movement sensors that measure movement of the musculature (not illustrated) in the face 107 of the subject 106, the computer 101 may function as a facial movement measuring and indicating device which receives electrical signals from the electrodes 110 in contact with the face 107. Accordingly, as illustrated in FIG. 2, the computer 101 with supporting software may be programmed to display a facial image 120 on the display 105 of the computer monitor 104. The computer 101 may additionally be programmed to convert the electrical output signals from the electrodes 110 into facial movement indications 121 and present the facial movement indications 121 on the facial image 120 in the areas of the facial image 120 which correspond to areas of muscle movement in the face 107 of the subject 106 in real time as sensed by the electrodes 110.

The strength of the electrical output signals that the computer 101 receives from the electrodes 110 may be proportional to the level or intensity of electrical nerve stimulation and therefore, the level or intensity of contraction of the musculature in the face 107 of the subject 106. Accordingly, the facial movement indications 121 may be adapted to visually differentiate the intensity of muscle movement in each area from the intensity of muscle movement in the other areas in the face 107 of the subject 106. As illustrated in FIG. 2, in some applications each facial movement indication 121 may be represented by one or multiple circles. Facial movement indications 121 having a single circle may indicate muscular contraction of relatively low-level intensity in the corresponding area or areas on the face 107, whereas facial movement indications 121 having multiple concentric circles of increasing number may indicate muscular contraction of correspondingly increasing intensity in the corresponding area or areas on the face 107. The information that is provided by the facial movement indications 121 may be used to formulate diagnoses and/or treatment of the subject 106 or may be used for other purposes.

In some embodiments, the facial movement sensors of the apparatus 100 may be accelerometers instead of the electrodes 110. Accordingly, the accelerometers may be attached to or secured into contact with the skin on the face 107 of the subject 106 or alternatively, surgically implanted in the face 107 in the same manner as was heretofore described with respect to the electrodes 110. The accelerometers sense movement of the muscles in the face 107 of the subject 106 and convert the movement of the muscles into electrical output signals that are transmitted to the computer 101 through the electrode wiring 111. The computer 101 may convert the electrical output signals into the facial movement indications 121, which may be presented on the facial image 120 displayed on the display 105 of the computer monitor 104.

In some applications, the apparatus 100 may electrically stimulate movement of muscles in the face 107 of the subject 106 for any of a variety of purposes. For example, the apparatus 100 may be used in therapeutic applications to enable or train the subject 106 to make facial movements or to assume facial expressions that accurately reflect the person's underlying thoughts and emotions, for example. In some therapeutic applications, the apparatus 100 may be used to train the subject 106 in changing facial expressions to accurately reflect the person's changing thoughts and emotions, for example. In some therapeutic applications, the apparatus 100 may be used to provide a low level stimulus, which causes sensory stimulation for regulation of emotions without causing firing of the muscles. In some therapeutic applications, the apparatus 100 may be used for clinical treatment of headaches, depression, anxiety and the like. In some applications, the apparatus 100 may be used to train a person in accurately mimicking or portraying facial expressions in response to staged situations as in the training of an actor, for example. Accordingly, in these applications the electrodes 110 may be placed on the face 107 of the subject 106 as was heretofore described with respect to the muscle movement measurement functions of the apparatus 100. The computer 101 with supporting software may function as an electrical input device which may be programmed to transmit electrical impulses to the electrodes 110 through the electrode wiring 111 in such a pattern and with such an intensity as to electrically stimulate and contract the musculature in the face 107 and induce the desired facial movements or expressions in the face 107 of the subject 106. In some applications, the computer 101 may be programmed to effect changing facial expressions in the face 107 of the subject 106 by changing the pattern and intensity of the electrical impulses that are transmitted to the electrodes 110.

Figure 3:
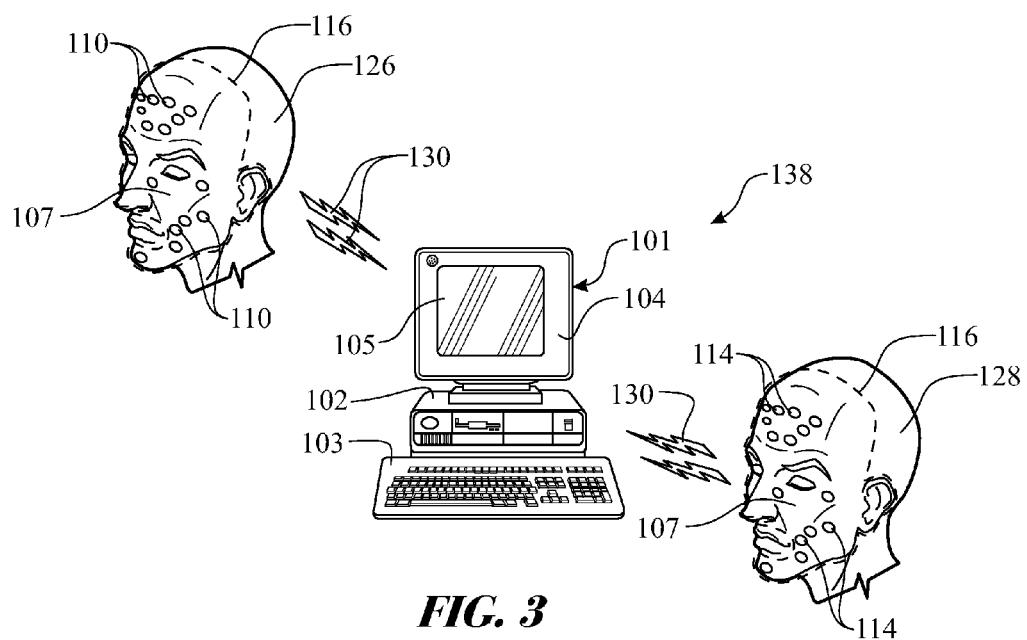
FIG. 3 illustrates implementation of an illustrative embodiment of the apparatus, in which facial movements are transferred or shared between two subjects via wireless communication with a computer.

Referring next to FIG. 3 of the drawings, an alternative illustrative embodiment of the facial movement measurement and stimulation apparatus is generally indicated by reference numeral 138. The apparatus 138 may be adapted to transfer voluntary or involuntary facial movements or expressions from a first subject 126 to a second subject 128 in any of a variety of applications. For example, in some applications the apparatus 138 may transfer voluntary facial movements or expressions from the first subject 126, who may be an acting trainer, to the second subject 128, who may be an actor-in-training. In such applications, the first subject 126 may use the apparatus 138 to train the second subject 128 to accurately mimic or portray facial expressions in response to various staged situations such as those which may occur during dramatic productions, for example. In some applications, the apparatus 138 may be used to facilitate the sharing of emotions between the first subject 126 and the second subject 128 via facial expressions.

The apparatus 138 may include a first set of electrodes 110 for placement on or surgical implantation in the face 107 of the first subject 126 and a second set of electrodes 114 for placement on or surgical implantation in the same corresponding areas on the face 107 of the second subject 128, either with or without the mask 116 as was heretofore described with respect to FIG. 1. The first set of electrodes 110 may function as facial movement sensors which sense movement of the various muscles in the face 107 of the first subject 126 via typically voluntary nerve-induced electrical stimulation of the facial muscles. In some embodiments, the facial movement sensors may be a set of accelerometers which are applied instead of the first set of electrodes 110 to the face 107 of the first subject 126 and which sense movement of the facial muscles. The second set of electrodes 114 may electrically stimulate movement of the various muscles in the face 107 of the second subject 128 according to the intensities and locations of the muscle movements in the face 107 of the first subject 126. Therefore, the computer 101 with supporting software may function as a stimulus transfer device which transfers the muscle movements in the face 107 of the first subject 126, received via the first set of electrodes 110, to the muscles in the face 107 of the second subject 128 via the second set of electrodes 114. In some embodiments, the first set of electrodes 110 and the second set of electrodes 114 may interface with the computer 101 via electrode wiring 111, as was heretofore described with respect to the apparatus 100 in FIG. 1. In other embodiments, the first set of electrodes 110 and the second set of electrodes 114 may interface with the computer 101 via wireless transmissions 130, as illustrated in FIG. 3, according to the knowledge of those skilled in the art.

The computer 101 with supporting software is adapted to receive electrical signals that correspond to typically voluntary, nerve-induced electrical stimulation of the musculature in the face 107 of the first subject 126 through the first set of electrodes 110. The computer 101 may be programmed to determine the locations and intensities of the electrical signals from the electrodes 110 on the various areas on the face 107 of the first subject 126 and transfer electrical impulses which correspond to the electrical signals to the second set of electrodes 114 which are applied to the corresponding areas on the face 107 of the second subject 128. The locations and intensities of the electrical impulses that are transmitted to the second set of electrodes 114 correspond to the locations and intensities of the electrical signals which were received from the first set of electrodes 110. Therefore, the electrical impulses which the second set of electrodes 114 applies to the muscles in the face 107 of the second subject 128 cause contraction of the respective facial muscles to effect the corresponding facial movements or expressions in the second subject 128 that were made by the first subject 126 as the first set of electrodes 110 transmitted the electrical signals to the computer 101. In some embodiments, the locations and intensities of the muscle movements in the face 107 of the first subject 126 may be indicated on the display 105 of the computer 101 such as in the form of the facial movement indications 121, as was heretofore described with respect to FIG. 2.

Figures 4, 5:
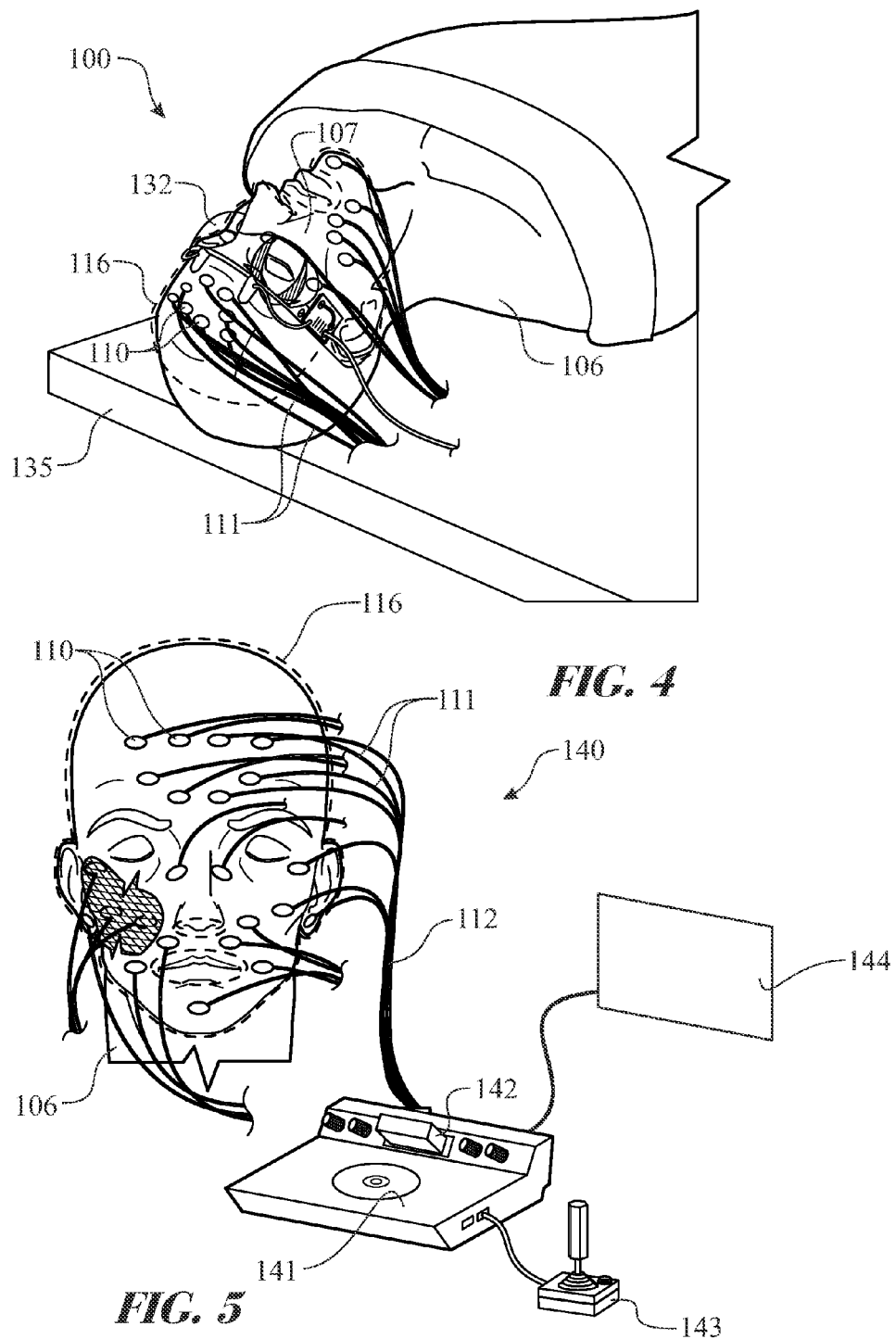
FIG. 4 is a perspective view of a subject lying on a support (partially in section), with multiple electrodes of an illustrative embodiment of the apparatus attached to the face of the subject and oculography glasses worn by the subject to monitor sleep phases.
FIG. 5 is a front view of an alternative illustrative embodiment of the apparatus (partially in section), with multiple electrodes attached to a face of a subject (shown in section) and the electrodes connected to a video game in implementation of the apparatus.

Referring next to FIG. 4 of the drawings, in an alternative application of the apparatus 100, which was heretofore described with respect to FIGS. 1 and 2, the electrodes 110 may be applied to the face 107 of a subject 106 as the subject 106 lies on a bed or other support 135. Oculography glasses 132 may be placed on the head of the subject 106 to record eye position and movements of the subject 106 such as in the analysis of various stages of sleep in the subject 106, for example. The stages of sleep can include both non-REM (Rapid Eye Movements) and REM sleep periods. Criteria for REM sleep include not only rapid eye movements, but also low muscle tone and a rapid, low voltage EEG. These features are easily discernible in a polysomnogram, the sleep study typically done for patients with suspected sleep disorders. Accordingly, in use of the apparatus 100, such as during sleep studies conducted on the subject 106, the computer 101 (FIG. 1) may function as a facial movement measuring and indicating device which receives from the electrodes 110 electrical signals that correspond to nerve-induced stimulation of the muscles in the face 107 of the subject 106 either through the electrode wiring 111, as shown, or via wireless transmissions 130 as was heretofore described with respect to FIG. 3. As was heretofore described with respect to FIG. 2, the computer 101 may be programmed to display a facial image 120 on the display 105 of the computer monitor 104 and present facial movement indications 121 on the areas of the facial image 120 which correspond to areas of muscle movement in the face 107 of the subject 106 in real time as sensed by the electrodes 110, as was heretofore described with respect to FIG. 1. The information that is revealed by the facial movement indications 121 on the facial image 120 and by the data received from the oculography glasses 132 may be used for diagnostic, therapeutic and/or other purposes. Additionally or alternatively, the computer 101 may be programmed to electrically stimulate the muscles in the face 107 of the subject 106 via the electrodes 110 for diagnostic, therapeutic and/or other purposes, as was heretofore described.

Referring next to FIG. 5 of the drawings, an alternative illustrative embodiment of the facial movement measurement and stimulation apparatus is generally indicated by reference numeral 140. The apparatus 140 may include a video game console 141 which may be adapted to receive one of various types of video game cartridges 142 for the playing of video games on a display 144 connected to the video game console 141. A joystick 143 may be connected to the video game console 142 to facilitate the movement of video game characters (not illustrated) on the display 144 as the video game is played. Electrodes 110 may interface with the video game console 141 via electrode wiring 111, as illustrated in FIG. 5, or alternatively, via wireless transmissions 130 (FIG. 3). The electrodes 110 are adapted for placement at various areas on the face 107 of a subject 106 either with or without the mask 116.

In some applications, the electrodes 110 may function as facial movement sensors which are adapted to sense facial movements or expressions of the subject 106 by measuring typically voluntary, nerve-induced electrical stimulation of the various muscles in the face 107 of the subject 106. The electrodes 110 may transmit electrical signals that correspond to the locations and intensities of the typically voluntary nerve-induced electrical stimulation of the facial muscles of the subject 106 to the video game console 141. The video game console 141 may be adapted to utilize the electrical signals from the electrodes 110 as audio components and/or as visual components of a video game on the display 144 as the video game is played by the subject 106 or by another. The facial movements or expressions of the subject 106 may be used to control one or more aspects or characters of the video game. In some applications, the video game console 141 may be adapted to transfer electrical impulses to the electrodes 110 to effect various facial movements in the face 107 of the subject 106 via electrical stimulation of the facial muscles. The facial movements which are induced in the face 107 of the subject 106 via the electrical impulses may correspond to facial or other movements which are made by a character presented on the display 144 as a video game is being played.

Figure 6:
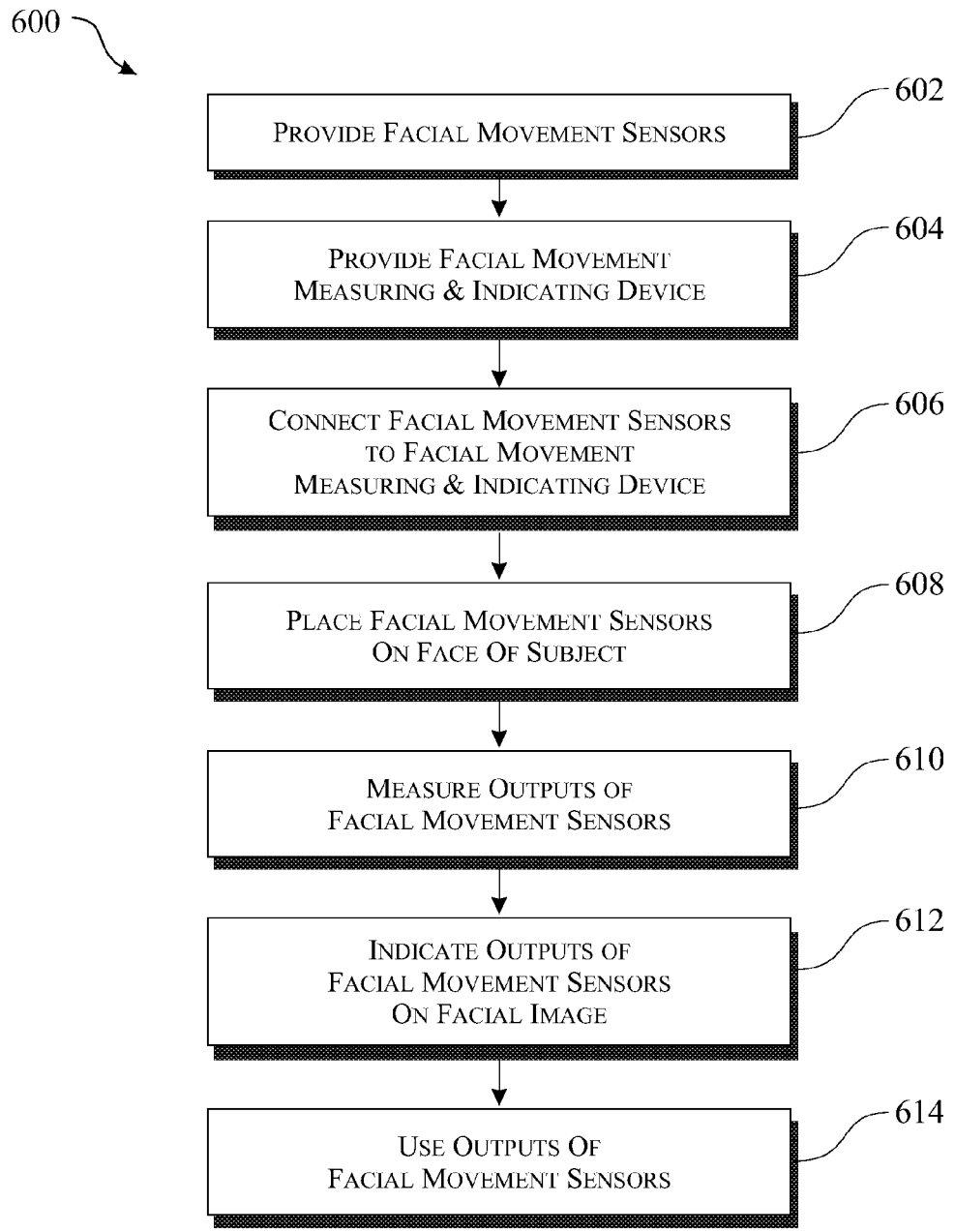
FIG. 6 is a flow diagram of an illustrative embodiment of a facial movement measurement method in which facial movements of a subject are measured.

Referring next to FIG. 6 of the drawings, a flow diagram of an illustrative embodiment of a facial movement measurement method is generally indicated by reference numeral 600. In block 602, facial movement sensors are provided. In some applications, the facial movement sensors may be electrodes. In some applications, the facial movement sensors may be accelerometers. In block 604, a facial movement measuring and indicating device is provided. In block 606, the facial movement sensors are connected to the facial movement measuring and indicating device. In block 608, the facial movement sensors are placed on or surgically implanted in the face of a subject. In block 610, outputs of the facial movement sensors in the form of electrical signals are measured. In block 612, the outputs of the facial movement sensors may be indicated on a facial image in the form of facial movement indications provided on a display. In block 614, the outputs of the facial movement sensors may be used for diagnostic, therapeutic and/or other purposes.

Figure 7:
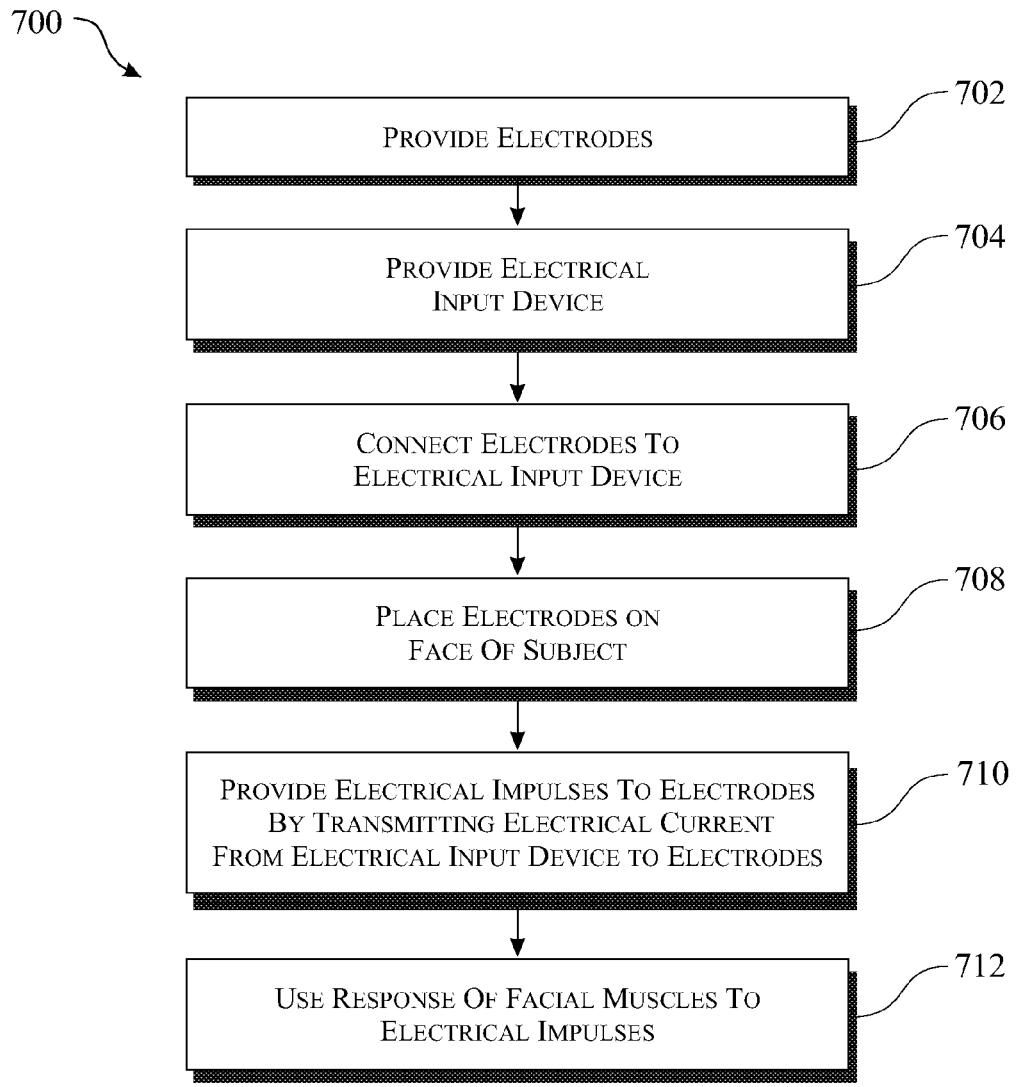
FIG. 7 is a flow diagram of an illustrative embodiment of a facial movement stimulation method in which facial movements are stimulated in a subject.

Referring next to FIG. 7 of the drawings, a flow diagram of an illustrative embodiment of a facial movement stimulation method is generally indicated by reference numeral 700. In block 702, electrodes are provided. In block 704, an electrical input device is provided. In block 706, the electrodes are connected to the electrical input device. In block 708, the electrodes are placed on or surgically implanted in the face of a subject. In block 710, electrical impulses are provided to the electrodes by transmitting an electrical current from the electrical input device to the electrodes. In block 712, the response of the facial muscles of the subject to the electrical impulses may be used for diagnostic, therapeutic and/or other purposes.

Figure 8:
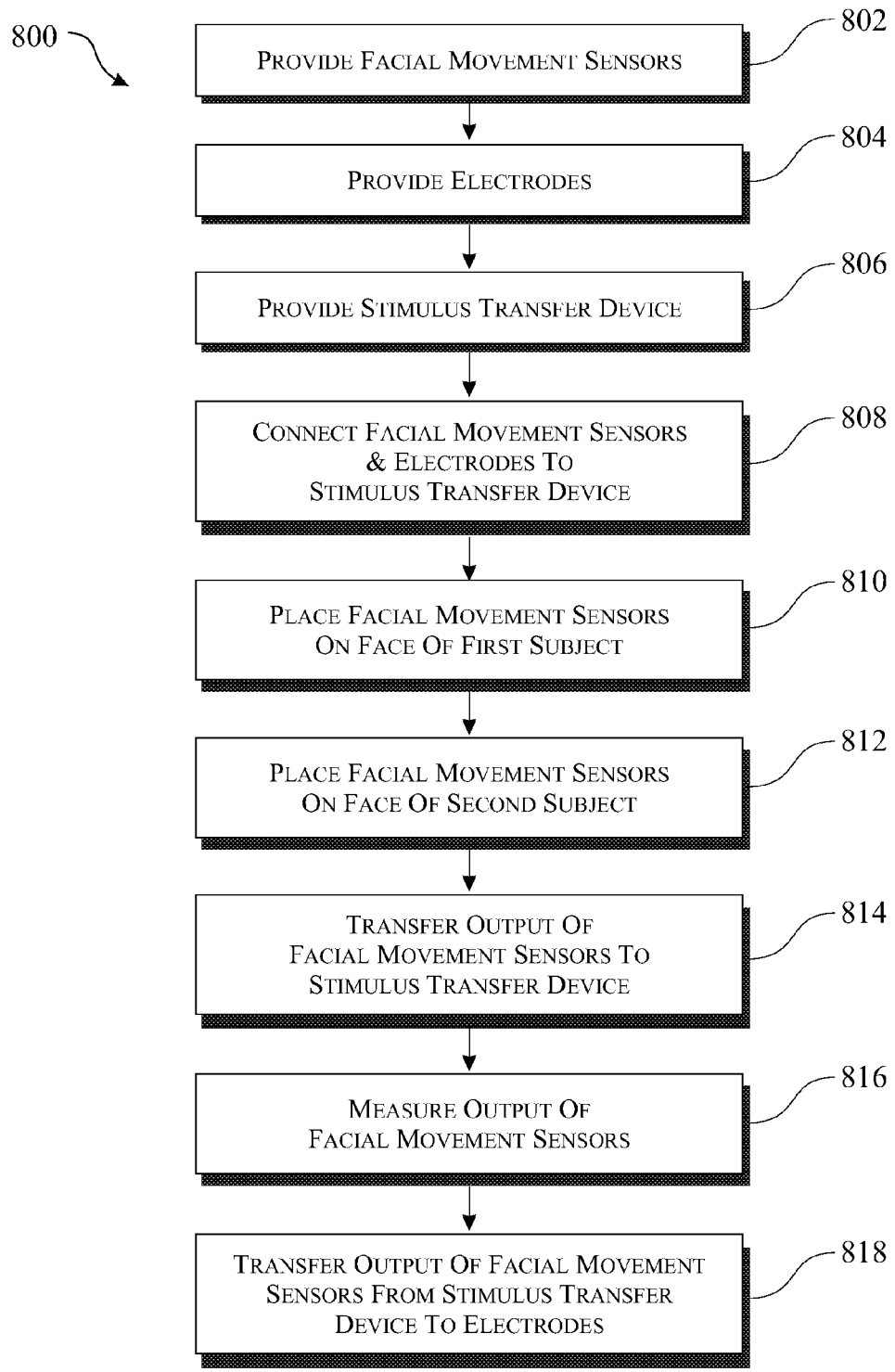
FIG. 8 is a flow diagram of an illustrative embodiment of a facial movement stimulation method in which facial movements are transferred from a first subject to a second subject.

Referring next to FIG. 8 of the drawings, a flow diagram of an illustrative embodiment of a facial movement stimulation method in which facial movements or expressions are transferred from a first subject to a second subject is generally indicated by reference numeral 800. In block 802, facial movement sensors are provided. In some applications, the facial movement sensors may be electrodes. In some applications, the facial movement sensors may be accelerometers. In block 804, electrodes are provided. In block 806, a stimulus transfer device is provided. In block 808, the facial movement sensors and the electrodes are connected to the stimulus transfer device. In block 810, the facial movement sensors are placed on or surgically implanted in the face of a first subject. In block 812, the electrodes are placed on or surgically implanted in the face of a second subject. In block 814, the output of the facial movement sensors, which may be in the form of electrical signals, is transferred to the stimulus transfer device. In block 816, the output of the facial movement sensors may be measured. In block 818, the output of the facial movement sensors may be transferred from the stimulus transfer device to the electrodes in the form of electrical impulses to effect the same facial movements or expressions in the second subject, as were made by the first subject.

Figure 9:
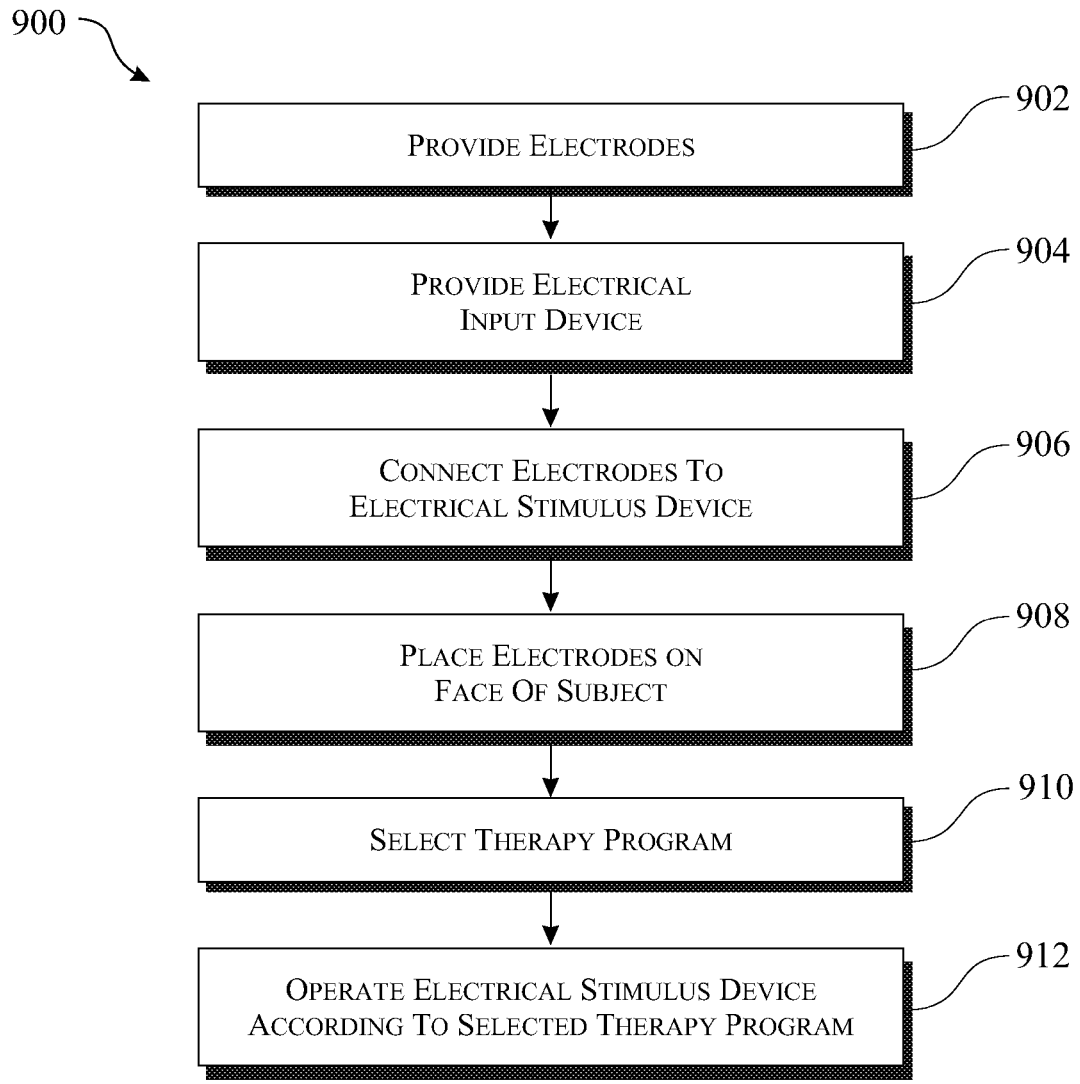
FIG. 9 is a flow diagram of an illustrative embodiment of a therapeutic facial movement stimulation method.

Referring next to FIG. 9 of the drawings, a flow diagram of an illustrative embodiment of a therapeutic facial movement stimulation method is generally indicated by reference numeral 900. In block 902, electrodes are provided. In block 904, an electrical stimulus device is provided. In block 906, the electrodes are connected to the electrical stimulus device. In block 908, the electrodes are placed on or surgically implanted in the face of a subject. In block 910, a therapy program is selected. In block 912, the electrical stimulus device is operated according to the selected therapy program to induce facial movements or expressions in the subject for therapeutic purposes. In some applications, the selected therapy program may be preprogrammed into a computer which may then automatically cycle through the electrical stimuli induced in the face of the subject to implement the therapy.

Figure 10:
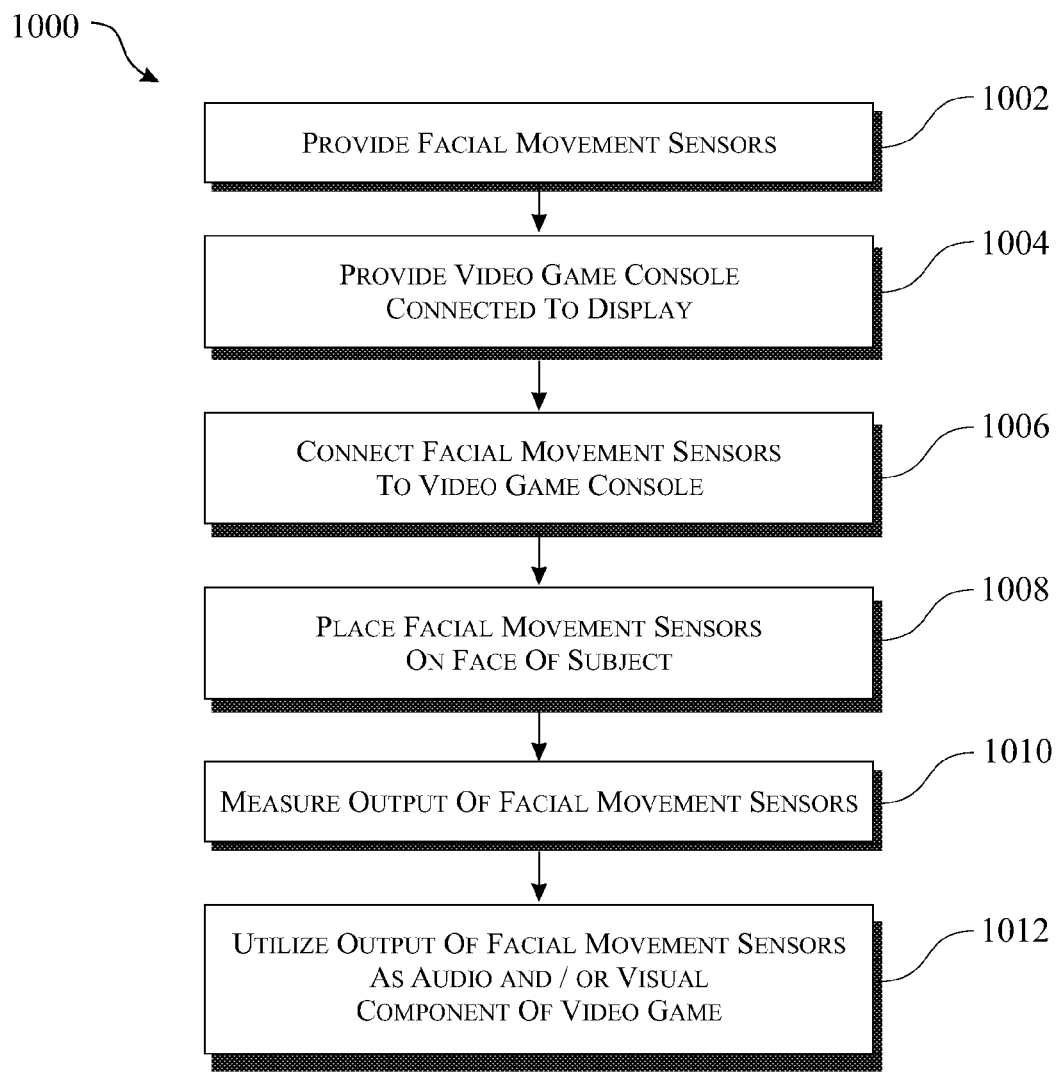
FIG. 10 is a flow diagram of an illustrative embodiment of a facial movement measurement method in which facial movements of a subject are utilised in a video game.

Referring next to FIG. 10, a flow diagram of an illustrative embodiment of a facial movement measurement method in which facial movements of a subject are utilised in a video game is generally indicated by reference numeral 1000. In block 1002, facial movement sensors are provided. In some applications, the facial movement sensors may be electrodes. In some applications, the facial movement sensors may be accelerometers. In block 1004, a video game console connected to a display is provided. In block 1006, the facial movement sensors are connected to the video game console. In block 1008, the facial movement sensors are placed on or surgically implanted in the face of a subject. In block 1010, the output of the facial movement sensors may be measured. In block 1012, the output of the facial movement sensors may be utilized as an audio and/or visual component of a video game that is played using the video game console.

Figure 11:
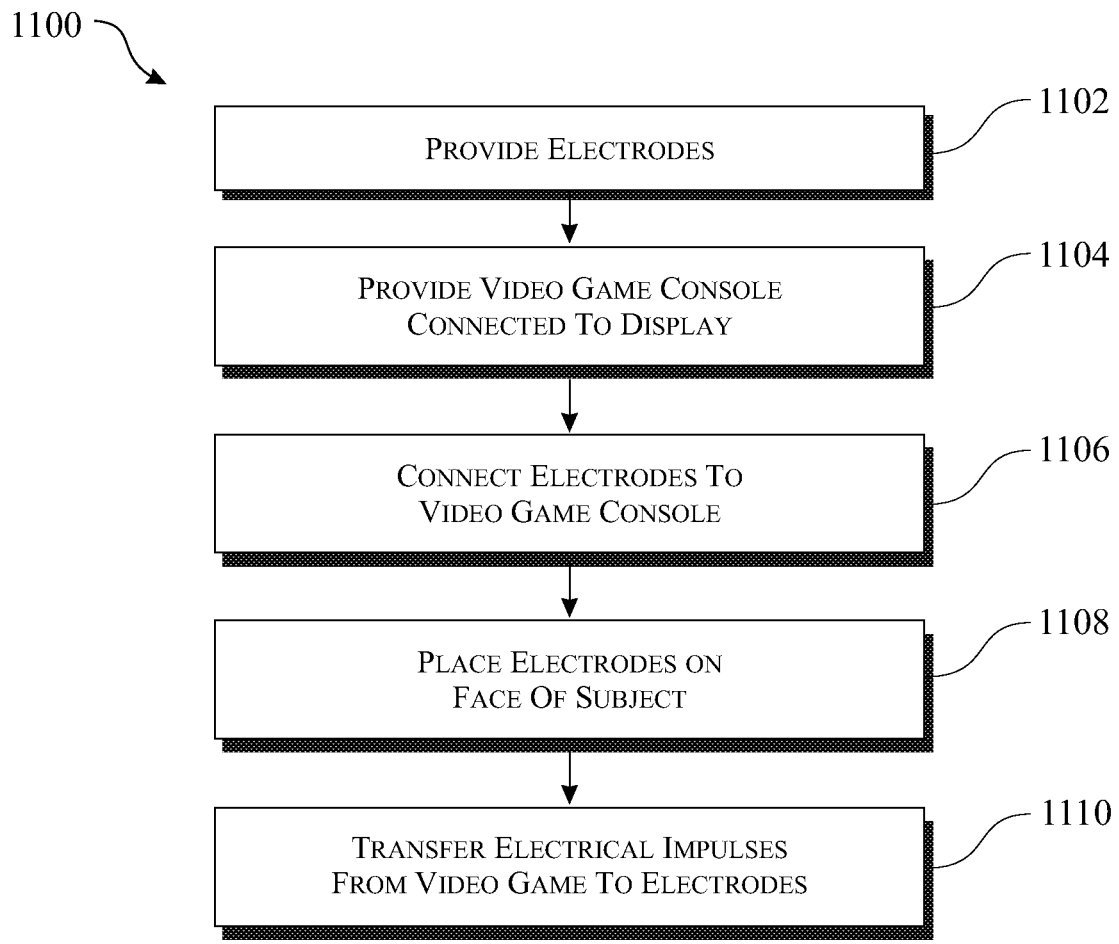
FIG. 11 is a flow diagram of an illustrative embodiment of the facial movement stimulation method in which electrical stimuli from a video game are transferred to a subject to effect facial movements in the subject.

Referring next to FIG. 11, a flow diagram of an illustrative embodiment of the facial movement stimulation method in which electrical stimuli from a video game are transferred to a subject to effect facial movements in the subject is generally indicated by reference numeral 1100. In block 1102, electrodes are provided. In block 1104, a video game console connected to a display is provided. In block 1106, the electrodes are connected to the video game console. In block 1108, the electrodes are placed on or surgically implanted in the face of a subject. In block 1110, electrical impulses are transferred from the video game console to the electrodes to induce facial movements or expressions in the subject. The facial movements or expressions which are induced in the face of the subject may correspond to facial or other movements or expressions which are made by a character presented on the display as a video game is being played using the video game console. In some applications, the facial movements or expressions of the subject may be used to control one or more aspects of the video game.

It will be appreciated by those skilled in the art that the apparatus and method in the various embodiments described herein above have numerous potential applications beyond those which are expressly described herein. For example, the apparatus and method may be used to study the contagiousness of emotions or the effect which changing facial expressions have on emotions in human subjects. In some applications, the apparatus and method may be used in mood intervention scenarios in which facial expressions that are indicative of positive emotions are transferred from one subject to another subject. The apparatus and method may be used as a polygraph in which facial twitches and movements may indicate whether a subject is lying in response to questioning. In some embodiments, the apparatus may be constructed with non-magnetic parts for use in conjunction with an MRI or other medical device.

Since many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence

What is claimed is:

1. An apparatus, comprising:
    at least one facial movement sensor, wherein said sensor is adapted to sense facial movement in a subject; and
    a facial movement measuring and indicating device interfacing with said at least one facial movement sensor, wherein said facial movement measuring and indicating device is adapted to receive said at least one signal from said at least one facial movement sensor, wherein said at least one signal is indicative of facial movement of the subject; and
    wherein said device comprises a computer including a computer disk drive and a computer monitor having a display, wherein said computer outputs facial movement indication signals to said computer monitor, and wherein said computer monitor visually presents on said display at least one image corresponding to said facial movement indication signals received by said computer.

2. The apparatus of claim 1 wherein said at least one facial movement sensor comprises at least one electrode, wherein said at least one electrode detects a nerve-induced electrical stimulation of a muscle in said subject's face and wherein said electrode transmits electrical output signals corresponding to said nerve-induced electrical stimulation to said computer.

3. The apparatus of claim 2 wherein said computer is a video game console adapted to receive said electrical output signals from said electrode as at least one of an audio component and a visual component of a video game as said video game is played by said subject.

4. The apparatus of claim 2 wherein said at least one image is a facial image having visual facial movement indications on said facial image in areas of said facial image that correspond to areas of said subject's face experiencing muscle movement, wherein said visual facial movement indications are updated by said computer in real-time as said at least one electrode detects said nerve-induced electrical stimulation of said muscle in said subject's face.

5. The apparatus of claim 1 wherein said at least one facial movement sensor comprises at least one accelerometer, wherein said accelerometer senses movement of a muscle in said subject's face and said accelerometer transmits electrical output signals corresponding to said movement to said computer.

6. The apparatus of claim 1 further comprising a mask and wherein said at least one facial movement sensor comprises a plurality of facial movement sensors that are carried by said mask.

7. The apparatus of claim 1 further comprising at least one electrode interfacing with said device and wherein said device is adapted to transmit at least one electrical impulse to said at least one electrode, wherein said electrode is in electrically-conductive contact with a skin of said subject's face and wherein a magnitude of said electrical impulse is effective to contract a muscle in said face.

8. The apparatus of claim 7 wherein said magnitude of said electrical impulse is varied to cause changing facial expressions in said subject's face.

9. The apparatus of claim 1 wherein said at least one facial movement sensor comprises a plurality of facial movement sensors, wherein said at least one of said plurality of facial movement sensors is located at each of a top portion, a middle portion, and a bottom portion of said subject's face, wherein said top portion corresponds to a subject's forehead area, and wherein said middle portion corresponds to a subject's eye and nose area, and wherein said bottom portion corresponds to a subject's mouth area.

10. The apparatus of claim 1 wherein said at least one image comprises a video game character.

11. An apparatus, comprising:
at least one electrode adapted to electrically stimulate facial muscular movement in a subject; and
a device interfacing with said at least one electrode, wherein said device is adapted to transmit at least one electrical impulse to said at least one electrode, wherein said electrode is in electrically-conductive contact with a skin of said subject's face and wherein a magnitude of said electrical impulse is effective to contract a muscle in said face.

12. The apparatus of claim 11 wherein said device comprises a video game console connected to a display, wherein said electrical impulse corresponds to a movement of a video game character presented on said display.

13. The apparatus of claim 11 further comprising a mask and wherein said at least one electrode comprises a plurality of electrodes that are carried by said mask.

14. The apparatus of claim 11 wherein said at least one electrode comprises a plurality of electrodes, wherein said at least one of said plurality of electrodes is located at each of a top portion, a middle portion, and a bottom portion of said subject's face, wherein said top portion corresponds to a subject's forehead area, and wherein said middle portion corresponds to a subject's eye and nose area, and wherein said bottom portion corresponds to a subject's mouth area.

15. A method of measuring and indicating facial movement in a subject, comprising:
providing at least one subject;
providing at least one facial movement sensor;
placing said at least one facial movement sensor on a face of said subject;
measuring an output of said at least one facial movement sensor; and
displaying a visual image corresponding to said facial movement in said subject;
further comprising providing a facial movement measuring and indicating device and connecting said at least one facial movement sensor to said facial movement measuring and indicating device and wherein said measuring and indicating an output of said at least one facial movement sensor comprises transmitting an electrical signal from said at least one facial movement sensor to said facial movement measuring and indicating device.

16. The method of claim 15 wherein said providing at least one facial movement measuring and indicating device comprises providing a video game console and wherein said measuring and indicating an output of said at least one facial movement sensor comprises transmitting an electrical signal from said at least one facial movement sensor to said video game console.

17. The method of claim 15 further comprising providing a second subject, providing at least one electrode on a face of said second subject and stimulating facial movement in said second subject by transmitting said output of said at least one facial movement sensor as an electrical impulse to said at least one electrode.

18. The method of claim 15 further comprising contracting a muscle in said face by transmitting at least one electrical impulse to at least one electrode, wherein said at least one electrode is in electrically-conductive contact with a skin of said face.

* * * * *